US011161809B2

(12) United States Patent
Xu et al.

(10) Patent No.: US 11,161,809 B2
(45) Date of Patent: Nov. 2, 2021

(54) PROCESSES FOR PREPARING 5-FLUORO-2-METHYL-1-(4-METHYLTHIOBENZYLIDENE)-3-INDANACETONITRILE AND FOR PREPARING SULINDAC

(71) Applicants: HANGZHOU NORMAL UNIVERSITY, Hangzhou (CN); HANGZHOU LOOP BIOTECH CO., LTD, Hangzhou (CN)

(72) Inventors: Weiming Xu, Hangzhou (CN); Wanmei Li, Hangzhou (CN); Lianzhi Tao, Hangzhou (CN); Pengfei Zhang, Hangzhou (CN); Hongyun Shen, Hangzhou (CN); Dongxiang Feng, Hangzhou (CN)

(73) Assignees: HANGZHOU NORMAL UNIVERSITY, Zhejiang (CN); HANGZHOU LOOP BIOTECH CO., LTD, Zhejiang (CN)

( * ) Notice: Subject to any disclaimer, the term of this patent is extended or adjusted under 35 U.S.C. 154(b) by 15 days.

(21) Appl. No.: 16/854,143

(22) Filed: Apr. 21, 2020

(65) Prior Publication Data
US 2021/0276947 A1 Sep. 9, 2021

(30) Foreign Application Priority Data
Mar. 3, 2020 (CN) .......................... 202010139316.4

(51) Int. Cl.
*C07C 315/02* (2006.01)
*C07C 253/22* (2006.01)
*C07C 317/46* (2006.01)
*C07C 255/35* (2006.01)

(52) U.S. Cl.
CPC .......... *C07C 315/02* (2013.01); *C07C 253/22* (2013.01); *C07C 255/35* (2013.01); *C07C 317/46* (2013.01); *C07C 2602/08* (2017.05)

(58) Field of Classification Search
None
See application file for complete search history.

(56) References Cited

PUBLICATIONS

Shuman et al. "A sterically efficient synthesis of (Z)-5-fluoro-2-methyl-1-(p-methylthiobenzylidene)-3-indenylacetic acid and its S-oxide, sulindac" J. Org. Chem., 1977, vol. 42, No. 11, 1914-1919.*

* cited by examiner

*Primary Examiner* — Joseph R Kosack

(57) ABSTRACT

The disclosure provides processes for preparing 5-fluoro-2-methyl-1-(4-methylthiobenzylidene)-3-indanacetonitrile and for preparing sulindac, relating to the field of medicine. The former comprises mixing 6-fluoro-2-methyl-1-indanone, cyanoacetic acid, a first organic solvent and an acetic acid-based catalyst to proceed with a first condensation reaction to give a first condensation reaction solution, which contains 5-fluoro-2-methyl-3-indanacetonitrile; and mixing the first condensation reaction solution, per se, with a base, a second organic solvent and 4-(methylthio)benzaldehyde to proceed with a second condensation reaction to give 5-fluoro-2-methyl-1-(4-methylthiobenzylidene)-3-indanacetonitrile. The process is a one-pot process without separation of 5-fluoro-2-methyl-3-indanacetonitrile from the solvent, shortening the synthetic route, simplifying the preparation process and improving the 5-fluoro-2-methyl-1-(4-methylthiobenzylidene)-3-indanacetonitrile yield.

20 Claims, 2 Drawing Sheets

PROCESSES FOR PREPARING 5-FLUORO-2-METHYL-1-(4-METHYLTHIOBENZYLIDENE)-3-INDANACETONITRILE AND FOR PREPARING SULINDAC

FIELD OF THE INVENTION

The present invention is related to the field of medicine, particularly to processes for preparing 5-fluoro-2-methyl-1-(4-methylthiobenzylidene)-3-indanacetonitrile and for preparing sulindac.

BACKGROUND OF THE INVENTION

Sulindac is a non-steroidal prodrug with little activity. It is metabolized to an active sulfide compound when ingested into human bodies, which is able to inhibit cyclooxygenase enzymes and reduce prostaglandin synthesis. So, sulindac has analgesic, anti-inflammatory, and antipyretic effects, and is used mainly to treat pain, rheumatoid arthritis, lumbago spondylitis, and gout arthritis. Further studies have shown that sulindac also has capacity to inhibit growth of tumor cells. Therefore, use of sulindac in tumor therapy has received extensive attention, and become a study hotspot in recent years.

A conventional process for synthesizing sulindac comprises condensing a key intermediate 6-fluoro-2-methylindanone with cyanoacetic acid, followed by decarboxylation and hydrolysis, to give 5-fluoro-2-methyl-3-indanacetic acid, which is separated from a solvent and then reacted with 4-(methylthio)benzaldehyde under a basic condition to give 5-fluoro-2-methyl-1-(4-methylthiobenzylidene)-3-indanacetic acid. This process is complex and has a long synthetic route.

SUMMARY OF THE INVENTION

In view of the above problems, an objective of the invention is to provide a process for preparing 5-fluoro-2-methyl-1-(4-methylthiobenzylidene)-3-indanacetonitrile and a process for preparing sulindac. The process for preparing 5-fluoro-2-methyl-1-(4-methylthiobenzylidene)-3-indanacetonitrile of the invention is a one-pot process, which is simple and has a short synthetic route.

Accordingly, an objective of the invention is realized by a process for preparing 5-fluoro-2-methyl-1-(4-methylthiobenzylidene)-3-indanacetonitrile, comprising:

mixing 6-fluoro-2-methyl-1-indanone, cyanoacetic acid, a first organic solvent and an acetic acid-based catalyst to proceed with a first condensation reaction to give a first condensation reaction solution, which contains 5-fluoro-2-methyl-3-indanacetonitrile; and mixing the first condensation reaction solution, per se, with a base, a second organic solvent and 4-(methylthio)benzaldehyde to proceed with a second condensation reaction to give 5-fluoro-2-methyl-1-(4-methylthiobenzylidene)-3-indanacetonitrile.

Preferably, the first condensation reaction may be carried out at about 100 to 140° C. for about 5 to 30 hours.

Preferably, the second condensation reaction may be carried out at about 50 to 90° C. for about 3 to 8 hours.

Preferably, the base may comprise one or more of: sodium hydroxide, sodium ethoxide, sodium methylate, potassium hydroxide, sodium hydride and potassium hydride.

Preferably, after the second condensation reaction is complete, a product of this reaction may be subjected to cooling, pH adjustment, layer separation, evaporation of an organic layer and purification sequentially.

The invention further provides a process for preparing sulindac, comprising:

Preparing 5-fluoro-2-methyl-1-(4-methylthiobenzylidene)-3-indanacetonitrile according to the above process of the invention, and mixing 5-fluoro-2-methyl-1-(4-methylthiobenzylidene)-3-indanacetonitrile with a solvent and a photocatalyst to proceed with a photo-catalytic oxidation and hydrolysis reaction under light irradiation to give sulindac, wherein, the photocatalyst is a metal chalcogenide nanomesh, the metal chalcogenide having a formula $MX_2$, where M represents one or more of Mo, W and V, and X represents one or more of S, Se and Te.

Preferably, after the photo-catalytic oxidation and hydrolysis reaction is complete, a product of this reaction may be subjected to a first filtration, distillation, a second filtration and purification.

Preferably, the photo-catalytic oxidation and hydrolysis reaction may be carried out at about 20 to 80° C. for about 2 to 12 hours.

Preferably, a mass ratio of the photocatalyst to 5-fluoro-2-methyl-1-(4-methylthiobenzylidene)-3-indanacetonitrile may be from about 0.5%: 1 to 3%: 1.

Preferably, the solvent may be an acetic acid solution with a mass ratio of acetic acid to water being from about 0.25:1 to 4:1.

The process for preparing 5-fluoro-2-methyl-1-(4-methylthiobenzylidene)-3-indanacetonitrile according to the invention comprises mixing 6-fluoro-2-methyl-1-indanone, cyanoacetic acid, a first organic solvent and an acetic acid-based catalyst to proceed with a first condensation reaction to give 5-fluoro-2-methyl-3-indanacetonitrile, and mixing 5-fluoro-2-methyl-3-indanacetonitrile with a base, a second organic solvent and 4-(methylthio)benzaldehyde to proceed with a second condensation reaction to give 5-fluoro-2-methyl-1-(4-methylthiobenzylidene)-3-indanacetonitrile. According to this process, no by-product is present in the first reaction solution as result of the first condensation reaction, and the pH of the solution and residual solvent would not affect the second condensation reaction. So, a one-pot process, which does not require separation of 5-fluoro-2-methyl-3-indanacetonitrile from the solvent, is employed to shorten the synthetic route, simplifying the preparation process and improving the yield of 5-fluoro-2-methyl-1-(4-methylthiobenzylidene)-3-indanacetonitrile. Results of examples show that the 5-fluoro-2-methyl-1-(4-methylthiobenzylidene)-3-indanacetonitrile yield provided by the process according to the invention is from about 82.4 to 88.4%.

The invention further provides a process for preparing sulindac comprising preparing 5-fluoro-2-methyl-1-(4-methylthiobenzylidene)-3-indanacetonitrile according to the above process of the invention, and mixing 5-fluoro-2-methyl-1-(4-methylthiobenzylidene)-3-indanacetonitrile with a solvent and a photocatalyst to proceed with a photo-catalytic oxidation and hydrolysis reaction under light irradiation to give sulindac. The photocatalyst is a metal chalcogenide nanomesh, the metal chalcogenide having a formula $MX_2$, where M represents one or more of Mo, W and V, and X represents one or more of S, Se and Te. According to this process, 5-fluoro-2-methyl-1-(4-methylthiobenzylidene)-3-indanacetonitrile is subjected to a photocatalytic oxidation and hydrolysis reaction in the presence of a photocatalyst under light irradiation. During this reaction, an E-isomer of 5-fluoro-2-methyl-1-(4-methylthiobenzylidene)-3-indanacetonitrile is converted into its Z-isomer which can be directly subjected to the photo-catalytic oxidation and hydrolysis reaction, improving the sulindac yield. So, with the invention, there is no need for separating the E-isomer, the stereochemical configuration about a carbon-carbon double bond in the sulindac molecule can be easily controlled, and the E-isomer yield is very low. Results of examples show that sulindac prepared by the process of the invention has a purity of over 99.5%, a yield of about 82.4 to 98.1%, and a mass ratio of the Z-isomer to the E-isomer of over 99:1.

DETAILED DESCRIPTION

Figure 1:
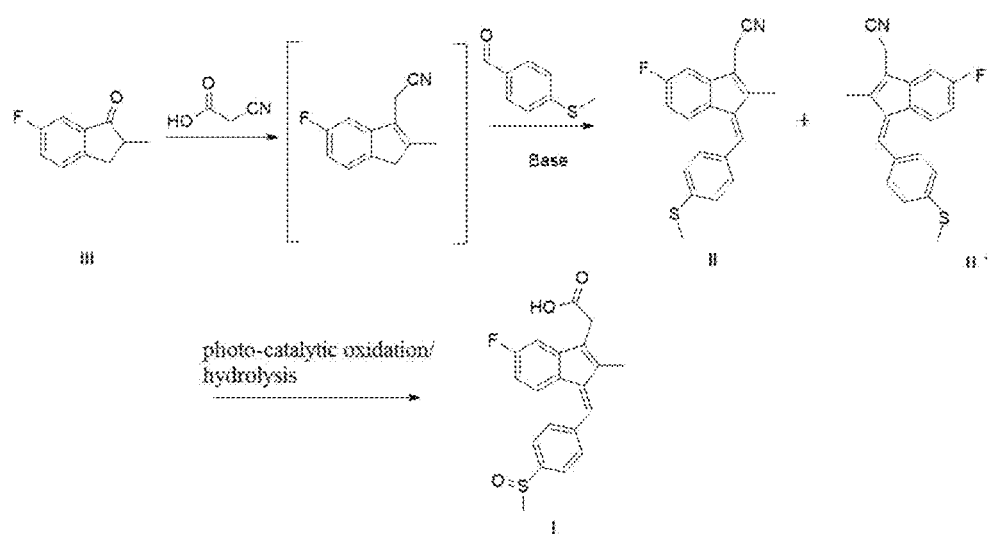
FIG. 1 shows a scheme for preparation of sulindac according to the invention.

The invention provides a process for preparing 5-fluoro-2-methyl-1-(4-methylthiobenzylidene)-3-indanacetonitrile, comprising:
mixing 6-fluoro-2-methyl-1-indanone, cyanoacetic acid, a first organic solvent and an acetic acid-based catalyst to proceed with a first condensation reaction to give a first condensation reaction solution, which contains 5-fluoro-2-methyl-3-indanacetonitrile; and
mixing the first condensation reaction solution, per se, with a base, a second organic solvent and 4-(methylthio) benzaldehyde to proceed with a second condensation reaction to give 5-fluoro-2-methyl-1-(4-methylthiobenzylidene)-3-indanacetonitrile.

The raw materials used according to the invention are commercially available products or can be prepared using conventional synthesis techniques well known to those of ordinary skill in the art, unless otherwise specified.

According to the process of the invention, 6-fluoro-2-methyl-1-indanone, cyanoacetic acid, a first organic solvent and an acetic acid-based catalyst are mixed to proceed with a first condensation reaction to give a first condensation reaction solution, which contains 5-fluoro-2-methyl-3-indanacetonitrile.

In some embodiments of the invention, the acetic acid-based catalyst may comprise one or more of: ammonium acetate, sodium acetate, acetic acid, and potassium acetate. In some embodiments, the first organic solvent may be toluene or xylene. In some embodiments, a molar ratio of 6-fluoro-2-methyl-1-indanone to cyanoacetic acid may be from about 1:1 to 1:2, preferably about 1:1.05. In some embodiments, a mass ratio of the first organic solvent to 6-fluoro-2-methyl-1-indanone may be from about 1:1 to 5:1, preferably about 1:1. In some embodiments, a molar ratio of the acetic acid-based catalyst to 6-fluoro-2-methyl-1-indanone may be from about 0.1:1 to about 0.3:1, preferably about 0.3:1.

In some embodiments, the first condensation reaction may be carried out at a temperature of about 100 to 140° C., preferably about 110 to 130° C. The first condensation reaction may be allowed to proceed for about 5 to 30 hours, preferably about 10 to 15 hours. Preferably, the first condensation reaction is carried out with removing water produced by the first reaction by fractional distillation.

According to the process of the invention, after the first condensation reaction solution is given, the first condensation reaction solution, per se, is mixed with a base, a second organic solvent and 4-(methylthio)benzaldehyde to proceed with a second condensation reaction to give 5-fluoro-2-methyl-1-(4-methylthiobenzylidene)-3-indanacetonitrile.

Preferably, after a temperature of the first condensation reaction solution is decreased to a temperature of about 50 to 90° C., the first condensation reaction solution, per se, may be mixed with the base, the second organic solvent and 4-(methylthio)benzaldehyde to proceed with the second condensation reaction. In some embodiments, a decrease rate of the temperature of the first condensation reaction solution may be from about 1 to 2° C./min. In some embodiments, the base may comprise one or more of: sodium hydroxide, sodium ethoxide, sodium methylate, potassium hydroxide, sodium hydride and potassium hydride. In an embodiment, the second organic solvent may be identical with the first organic solvent, whereby a detail explanation thereof is omitted. In some embodiments, a mass ratio of the second organic solvent to 6-fluoro-2-methyl-1-indanone may be from about 1:1 to 3:1, preferably from about 1:1 to 2.6:1. In some embodiments, a molar ratio of 4-(methylthio)benzaldehyde to 6-fluoro-2-methyl-1-indanone may be from about 1:1 to 2:1, preferably about 1.1:1.

In some embodiments, the second condensation reaction may be carried out at a temperature of from about 50 to 90° C., preferably from about 65 to 70° C. The second condensation reaction may be allowed to proceed for about 3 to 8 hours, preferably about 4 to 5 hours. In some embodiments, a molar ratio of the base to 6-fluoro-2-methyl-1-indanone may be from about 1:1 to 3:1, preferably about 1:1 to 2:1.

After the second condensation reaction is complete, a second condensation reaction solution obtained may be preferably subjected to cooling, pH adjustment, layer separation, evaporation of an organic layer, and purification sequentially to give 5-fluoro-2-methyl-1-(4-methylthiobenzylidene)-3-indanacetonitrile.

In an embodiment, a cooling medium for cooling the second condensation reaction solution may be ambient-temperature water. In an embodiment, hydrochloric acid, preferably with a concentration of 0.1M, is preferably used as a pH adjusting agent for adjusting the pH of the cooled second condensation reaction solution. The amount of the pH adjusting agent for use in the invention is not specifically restricted provided that the pH of the cooled second condensation reaction solution can be adjusted to about 6.5 to 7.5, preferably about 6.5 to 7. The organic layer or phase is preferably separated by liquid-liquid layer or phase separation, and the layer separation step is not particular limited and may be carried out in manners well known to those of ordinary skill in the art. In some embodiments, the organic layer may be evaporated at about 90 to 140° C. to dryness, preferably at about 110 to 120° C. In some embodiments, the evaporation step may be performed for about 0.5 to 1 h. The evaporation step is not particular limited and may be carried out in manners well known to those of ordinary skill in the art. In an embodiment, a product obtained by evaporating the organic layer may be purified by recrystallization in ethyl acetate. In some embodiments, a mass ratio of the product obtained by evaporating the organic layer to ethyl acetate may be in a range of from about 1:1 to 5:1, preferably from about 1:1 to 3:1. In an embodiment, the recrystallization may be carried out in a protective gas atmosphere. In an embodiment, a recrystallization temperature may be in a range of from about 60 to 80° C., and a recrystallization time may be in a range of about 2 to 5 hours. The recrystallization step is not particular limited and may be carried out in manners well known to those of ordinary skill in the art. The process of the invention is carried out in a one-pot process to prepare key intermediate 5-fluoro-2-methyl-1-(4-methylthiobenzylidene)-3-indanacetonitrile and improves its yield.

The invention further provides a process for preparing sulindac, comprising: preparing 5-fluoro-2-methyl-1-(4-methylthiobenzylidene)-3-indanacetonitrile according to the above process of the invention, and mixing 5-fluoro-2-methyl-1-(4-methylthiobenzylidene)-3-indanacetonitrile with a solvent and a photocatalyst to proceed with a photo-catalytic oxidation and hydrolysis reaction under light irradiation to give sulindac, wherein, the photocatalyst is a metal chalcogenide nanomesh, the metal chalcogenide having a formula $MX_2$, where M represents one or more of Mo, W and V, and X represents one or more of S, Se and Te.

According to the process of the invention, after 5-fluoro-2-methyl-1-(4-methylthiobenzylidene)-3-indanacetonitrile is obtained, it is mixed with a solvent and a photocatalyst to proceed with a photo-catalytic oxidation and hydrolysis reaction under light irradiation to give sulindac.

According to the process of the invention, the photocatalyst is a metal chalcogenide nanomesh, the metal chalcogenide having a formula $MX_2$, where M represents one or more of Mo, W and V, and X represents one or more of S, Se and Te. When M represents a mixture of Mo and W, a mass ratio of Mo to W may be preferably from about 1:5 to 1:0.2. When M represents a mixture of Mo and V, a mass ratio of Mo to V may be preferably from about 1:5 to 1:0.2. When M represents a mixture of W and V, a mass ratio of W to V may be preferably from about 1:5 to 1:0.2. When M represents a mixture of Mo, W and V, a mass ratio of Mo:W:V may be preferably about 1:0.2~5:0.2~5. When X represents a mixture of S and Se, a mass ratio of S to Se may be preferably from about 1:5 to 1:0.2. When X represents a mixture of S and Te, a mass ratio of S to Te may be preferably from about 1:5 to 1:0.2. When X represents a mixture of Se and Te, a mass ratio of Se to Te may be preferably from about 1:5 to 1:0.2. When X represents a mixture of S, Se and Te, a mass ratio of S:Se:Te may be preferably about 1:0.2~5:0.2~5. In some embodiments, the photocatalyst may preferably have a particle size of about 50 to 200 nanometers. In some embodiments, the photocatalyst may preferably have an inter-structure spacing of about 2 to 10 nanometers.

In an embodiment of the invention, a preferred process for preparation of the photocatalyst is a baking process, for example described in "2D Single Crystal $WSe_2$ and $MoSe_2$ Nanomeshes with Quantifiable High Exposure of Layer Edges from 3D Mesoporous Silica Template, ACS Appl. Mater. Interfaces, 2019, 11, 17670-17677" (see paragraphs 1-2 in EXPERIMENTAL SECTION on pages 17675 to 17676). There are a large number of reactive dangling bonds among atoms around a lattice layer of the photocatalyst used in the process of the invention, which, under light irradiation, provides energy of a specific strength for inversion of an E-isomer of 5-fluoro-2-methyl-1-(4-methylthiobenzylidene)-3-indanacetonitrile, allowing the E-isomer to be inverted into its Z-isomer. The Z-isomer is then subjected to the photo-catalytic oxidation and hydrolysis reaction. So, the sulindac yield is improved.

In an embodiment of the invention, the solvent may be an acetic acid solution. Preferably, a mass ratio of acetic acid to water may be from about 0.25:1 to 4:1, further preferably from about 1:1 to 2:1. The mass ratio of acetic acid to water ensures that no by-product is produced during the reaction, which improves the sulindac yield. In an embodiment, a mass ratio of the photocatalyst to 5-fluoro-2-methyl-1-(4-methylthiobenzylidene)-3-indanacetonitrile may be from about 0.5%: 1 to 3%: 1, preferably from about 0.5%: 1 to 1%: 1. In an embodiment, a mass ratio of the solvent to 5-fluoro-2-methyl-1-(4-methylthiobenzylidene)-3-indanacetonitrile may be from about 5:1 to 15:1, preferably from about 8:1 to 10:1.

In an embodiment, a temperature of the photo-catalytic oxidation and hydrolysis reaction may be from about 20 to 80° C., preferably from about 30 to 50° C. In an embodiment, the photo-catalytic oxidation and hydrolysis reaction may be carried out for about 2 to 12 hours, preferably about 3 to 6 hours.

After the photo-catalytic oxidation and hydrolysis reaction is complete, a product of this reaction may be preferably subjected to a first filtration, distillation, a second filtration, and purification to obtain the sulindac.

In an embodiment, after the first filtration, the photocatalyst and a filtrate containing the product of the photocatalytic oxidation and hydrolysis reaction may be obtained. The first filtration step is not particular limited and may be carried out in manners well known to those of ordinary skill in the art. In an embodiment, the photocatalyst obtained may be recovered. In an embodiment, the product of the photo-catalytic oxidation and hydrolysis reaction may be further subjected to distillation. The distillation may be preferably carried out at about 80 to 120° C., preferably about 95 to 110° C., for about 1 to 2 hours. In an embodiment, the product may be distilled until no solvent is distilled off, to obtain the solvent and crude sulindac. The distillation step is not particular limited and may be carried out in manners well known to those of ordinary skill in the art. In an embodiment, the solvent may be recovered. In an embodiment, crude sulindac may be subjected to a second filtration to obtain a filter cake containing crude sulindac and a filtrate. The second filtration step is not particular limited and may be carried out in manners well known to those of ordinary skill in the art. In an embodiment, the filtrate may be discarded. Preferably, the crude sulindac may be purified to obtain pure sulindac. In an embodiment, the crude sulindac may be added into isopropanol for recrystallization to realize the purification. In an embodiment, the recrystallization may be carried out under a protective gas atmosphere. In an embodiment, the recrystallization may be carried out at about 60 to 90° C. for about 2 to 5 hours. In an embodiment, a mass ratio of isopropanol to the crude sulindac may be from about 4:1 to 10:1, preferably from about 6:1 to 8:1.

FIG. 1 shows a scheme for preparation of sulindac according to the invention. 6-fluoro-2-methyl-1-indanone (III) and cyanoacetic acid are subjected to a condensation reaction in the presence of a catalyst, to give 5-fluoro-2-methyl-3-indanacetonitrile, which is then subjected to a further condensation reaction with 4-(methylthio)benzaldehyde in the presence of a base to give 5-fluoro-2-methyl-1-(4-methylthiobenzylidene)-3-indanacetonitrile of Z (II) and E (II') configurations. The E-isomer is then converted to the Z-isomer under light irradiation, which is then directly subjected to a photocatalytic oxidation and hydrolysis reaction to give sulindac (I). Hereinafter, the present invention is described in more detail by reference to examples, but the present invention is not limited to these examples.

Example 1

164 g of 6-fluoro-2-methylindanone, 100 g of cyanoacetic acid, 8.2 g of sodium acetate, and 328 g of xylene were introduced into a reaction vessel fitted with a thermometer, a stirrer, and a water separator. During the reaction, the reaction temperature was controlled at 50° C., and the reaction was carried out with removing water produced by the reaction by fractional distillation from the reaction system. After 5 hours of reaction, the reaction solution was cooled to 50° C., and 36 g of sodium hydride and 164 g of 4-(methylthio)benzaldehyde were then added into the reaction solution. The reaction solution was kept at 90° C. for 3 hours, then adjusted to neutral with 0.1 M hydrochloric acid and subjected to layer separation. An organic layer formed was evaporated at 135° C. for 1 h to dryness. A crude product obtained was recrystallized in 500 g of ethyl acetate at 78° C. for 4 h to obtain 283.8 g of 5-fluoro-2-methyl-1-(4-methylthiobenzylidene)-3-indanacetonitrile with a yield of 88.4%.

1.64 g of ammonium molybdate and 0.36 g of ammonium metatungstate were dissolved in 8 g of water to form a solution. 10 g of the solution, 10 g of a mesoporous material SBA-15, and 200 mL of n-hexane were introduced into a reaction vessel. This mixture was stirred at room temperature for 3 hours followed by filtration and oven dried to obtain 12 g of a powder. 12 g of the powder was mixed with 12 g of tellurium powder. This mixture was introduced into a tube furnace, and subjected to a reduction reaction at 700° C. for 2 hours with hydrogen being introduced into the furnace (with a hydrogen flow rate of 200 mL/min). A solid obtained was added into 100 mL of 30% HF solution. The solution was stirred at 25° C. for 2 hours, and then filtered to obtain a solid. After drying the solid, 4.16 g of a catalyst was obtained. 50 g of 5-fluoro-2-methyl-1-(4-methylthiobenzylidene)-3-indanacetonitrile, 0.5 g of the $Mo_3WTe_8$ catalyst, and 500 g of 50 wt % acetic acid aqueous solution were introduced into a reaction vessel to proceed with a reaction at 80° C. for 2 hours under visible light irradiation. At the end of the reaction, the catalyst was recovered by filtration, and the solvent in a filtrate obtained was recovered by distillation. The distillation was carried out at 110° C. for 1 h, precipitating a crude product. The crude product was subjected to filtration to give a filter cake. The filter cake was recrystallized in isopropanol at 82° C. for 4 hours, to give 51.2 g of sulindac with a purity of 99.5% and a yield of 92.3%. A mass ratio of the Z-isomer of the sulindac product to its E-isomer was Z/E=99.3:1.

Figure 4:
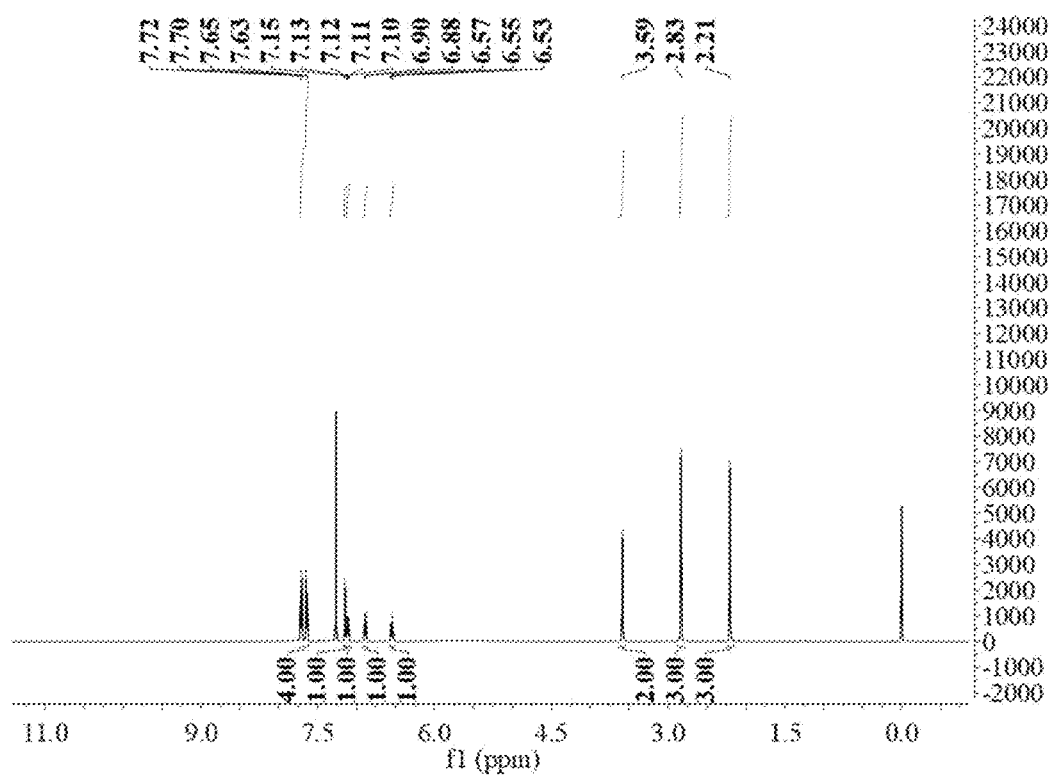
FIG. 4 shows $^1$H-NMR spectrum of sulindac prepared in example 1.

FIG. 4 shows $^1$H-NMR spectrum of sulindac produced in example 1, where $^1$H NMR (500 MHz, $CDCl_3$) δ 7.68 (dd, J=36.7, 8.0 Hz, 4H), 7.15 (s, 1H), 7.11 (dd, J=8.2, 5.1 Hz, 1H), 6.89 (d, J=8.8 Hz, 1H), 6.55 (t, J=8.7 Hz, 1H), 3.59 (s, 2H), 2.83 (s, 3H), 2.21 (s, 3H).

Figure 2:
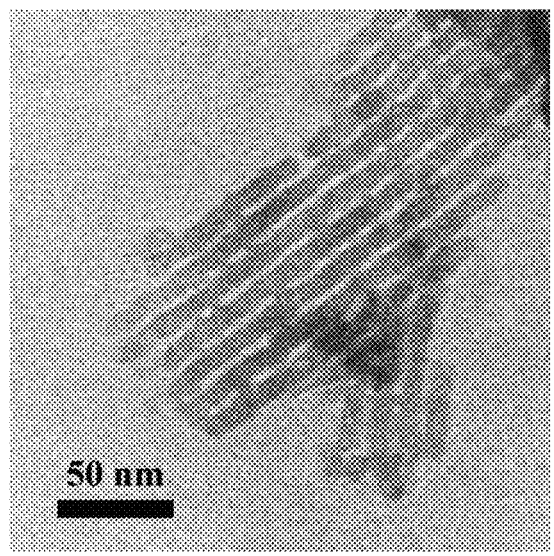
FIG. 2 shows a transmission electron micrograph of a molybdenum selenide photocatalyst prepared in example 1.
Figure 3:
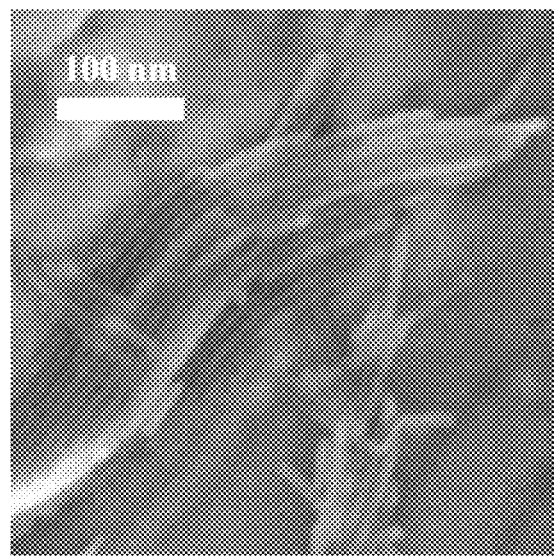
FIG. 3 shows a scanning electron micrograph of the molybdenum selenide photocatalyst prepared in example 1.

FIG. 2 shows a transmission electron micrograph of the molybdenum selenide photocatalyst prepared in example 1, and FIG. 3 shows a scanning electron micrograph thereof. From FIGS. 2 and 3, it can be seen that there are a large number of reactive dangling bonds among atoms around a lattice layer of the molybdenum selenide photocatalyst, which provides a large number of active sites for inversion of the E-isomer under light irradiation.

Example 2

164 g of 6-fluoro-2-methylindanone, 170 g of cyanoacetic acid, 8.2 g of sodium acetate, 12 g of acetic acid, and 2460 g of toluene were introduced into a reaction vessel fitted with a thermometer, a stirrer, and a water separator. During the reaction, the reaction temperature was controlled at 100° C., and the reaction was carried out with removing water produced by the reaction by fractional distillation from the reaction system. After 30 hours of reaction, the reaction solution was cooled to 50° C., and 72 g of sodium hydride and 304 g of 4-(methylthio)benzaldehyde were then added into the reaction solution. The reaction solution was kept at 50° C. for 8 hours, then adjusted to neutral with 0.1 M hydrochloric acid and subjected to layer separation. An organic layer formed was evaporated at 110° C. for 1 h to dryness. A crude product obtained was recrystallized in 500 g of ethyl acetate at 78° C. for 4 h to obtain 264.5 g of 5-fluoro-2-methyl-1-(4-methylthiobenzylidene)-3-indanacetonitrile with a yield of 82.4%. 2.0 g of ammonium molybdate was dissolved in 8 g of water to form a solution. 10 g of the solution, 10 g of a mesoporous material SBA-15, and 200 mL of n-hexane were introduced into a reaction vessel. This mixture was stirred at room temperature for 3 hours followed by filtration and oven dried to obtain 12 g of a powder. 12 g of the powder was mixed with 12 g of tellurium powder. This mixture was introduced into a tube furnace, and subjected to a reduction reaction at 700° C. for 2 hours with hydrogen being introduced into the furnace (with a hydrogen flow rate of 200 mL/min). A solid obtained was added into 100 mL of 30% HF solution. The solution was stirred at 25° C. for 2 hours, and then filtered to obtain a solid. After drying the solid, 2.59 g of a catalyst was obtained.

50 g of 5-fluoro-2-methyl-1-(4-methylthiobenzylidene)-3-indanacetonitrile, 0.25 g of the $MoSe_2$ catalyst, and 250 g of 80 wt % acetic acid aqueous solution were introduced into a reaction vessel to proceed with a reaction at 80° C. for 12 hours under visible light irradiation. At the end of the reaction, the catalyst was recovered by filtration, and the solvent in a filtrate obtained was recovered by distillation. The distillation was carried out at 110° C. for 1 h, precipitating a crude product. The crude product was subjected to filtration to give a filter cake. The filter cake was recrystallized in 80 g of isopropanol at 82° C. for 4 hours, to give 50.2 g of sulindac with a purity of 99.7% and a yield of 90.5%. A mass ratio of the Z-isomer of the sulindac product to its E-isomer was Z/E=99.1:1.

Example 3

164 g of 6-fluoro-2-methylindanone, 85 g of cyanoacetic acid, 6 g of acetic acid, and 820 g of xylene were introduced into a reaction vessel fitted with a thermometer, a stirrer, and a water separator. During the reaction, the reaction temperature was controlled at 130° C., and the reaction was carried out with removing water produced by the reaction by fractional distillation from the reaction system. After 20 hours of reaction, the reaction solution was cooled to 50° C., and 24 g of sodium hydride and 152 g of 4-(methylthio)benzaldehyde were then added into the reaction solution. The reaction solution was kept at 50° C. for 8 hours, then adjusted to neutral with 0.1 M hydrochloric acid and subjected to layer separation. An organic layer formed was evaporated at 135° C. for 1 h to dryness. A crude product obtained was recrystallized in 500 g of ethyl acetate at 78° C. for 4 h to obtain 266.6 g of 5-fluoro-2-methyl-1-(4-methylthiobenzylidene)-3-indanacetonitrile with a yield of 83.1%.

2.0 g of ammonium molybdate was dissolved in 8.0 g of water to form a solution. 10 g of the solution, 10 g of a SBA-15 mesoporous material, and 200 mL of n-hexane were introduced into a reaction vessel. This mixture was stirred at room temperature for 3 hours followed by filtration and oven dried to obtain 12 g of a powder. 12 g of the powder was mixed with 12 g of tellurium powder. This mixture was introduced into a tube furnace, and subjected to a reduction reaction at 700° C. for 2 hours with hydrogen being introduced into the furnace (with a hydrogen flow rate of 200 mL/min). A solid obtained was added into 100 mL of 30% HF solution. The solution was stirred at 25° C. for 2 hours, and then filtered to obtain a solid. After drying the solid, 2.59 g of a catalyst was obtained.

50 g of 5-fluoro-2-methyl-1-(4-methylthiobenzylidene)-3-indanacetonitrile, 1.5 g of the $MoSe_2$ catalyst, 750 g of 20 wt % acetic acid aqueous solution were introduced into a reaction vessel to proceed with a reaction at 20 to 25° C. for 12 hours under visible light irradiation. At the end of the reaction, the catalyst was recovered by filtration, and the solvent in a filtrate obtained was recovered by distillation. The distillation was carried out at 110° C. for 1 h, precipitating a crude product. The crude product was subjected to filtration to give a filter cake. The filter cake was recrystallized in 80 g of isopropanol at 82° C. for 4 hours, to give 54.1 g of sulindac with a purity of 99.6% and a yield of 97.6%. A mass ratio of the Z-isomer of the sulindac product to its E-isomer was Z/E=99.3:1.

Example 4

164 g of 6-fluoro-2-methylindanone, 100 g of cyanoacetic acid, 10 g of ammonium acetate, and 1000 g of xylene were introduced into a reaction vessel fitted with a thermometer, a stirrer, and a water separator. During the reaction, the reaction temperature was controlled at 120° C., and the reaction was carried out with removing water produced by the reaction by fractional distillation from the reaction system. After 10 hours of reaction, the reaction solution was cooled to 50° C., and 54 g of sodium methylate, 4 g of sodium hydroxide and 160 g of 4-(methylthio)benzaldehyde were then added into the reaction solution. The reaction solution was kept at 70° C. for 5 hours, then adjusted to neutral with 0.1 M hydrochloric acid and subjected to layer separation. An organic layer formed was evaporated at 135° C. for 1 h to dryness. A crude product obtained was recrystallized in 500 g of ethyl acetate at 78° C. for 4 h to obtain 266.0 g of 5-fluoro-2-methyl-1-(4-methylthiobenzylidene)-3-indanacetonitrile with a yield of 82.9%.

1.0 g of ammonium metavanadate was dissolved in 9.0 g of hot water to form a solution. 10 g of the solution, 10 g of a SBA-15 mesoporous material, and 200 mL of n-hexane were introduced into a reaction vessel. This mixture was stirred at room temperature for 3 hours followed by filtration and oven dried to obtain 11 g of a powder. 11 g of the powder was mixed with 11 g of tellurium powder. This mixture was introduced into a tube furnace, and subjected to a reduction reaction at 700° C. for 2 hours with hydrogen being introduced into the furnace (with a hydrogen flow rate of 200 mL/min). A solid obtained was added into 100 mL of 30% HF solution. The solution was stirred at 25° C. for 2 hours, and then filtered to obtain a solid. After drying the solid, 1.78 g of a catalyst was obtained.

50 g of 5-fluoro-2-methyl-1-(4-methylthiobenzylidene)-3-indanacetonitrile, 1.0 g of the $VSe_2$ catalyst, 500 g of 40 wt % acetic acid aqueous solution were introduced into a reaction vessel to proceed with a reaction at 40 to 45° C. for 4 hours under visible light irradiation. At the end of the reaction, the catalyst was recovered by filtration, and the solvent in a filtrate obtained was recovered by distillation. The distillation was carried out at 110° C. for 1 h, precipitating a crude product. The crude product was subjected to filtration to give a filter cake. The filter cake was recrystallized in 80 g of isopropanol at 82° C. for 4 hours, to give 52.4 g of sulindac with a purity of 99.5% and a yield of 94.5%. A mass ratio of the Z-isomer of the sulindac product to its E-isomer was Z/E=99.3:1.

Example 5

164 g of 6-fluoro-2-methylindanone, 100 g of cyanoacetic acid, 10 g of ammonium acetate, and 1000 g of xylene were introduced into a reaction vessel fitted with a thermometer, a stirrer, and a water separator. During the reaction, the reaction temperature was controlled at 135° C., and the reaction was carried out with removing water produced by the reaction by fractional distillation from the reaction system. After 10 hours of reaction, the reaction solution was cooled to 50° C., and 68 g of sodium ethoxide, 6 g of potassium hydroxide and 160 g of 4-(methylthio)benzaldehyde were then added into the reaction solution. The reaction solution was kept at 60° C. for 6 hours, then adjusted to neutral with 0.1 M hydrochloric acid and subjected to layer separation. An organic layer formed was evaporated at 135° C. for 1 h to dryness. A crude product obtained was recrystallized in 500 g of ethyl acetate at 78° C. for 4 h to obtain 268.9 g of 5-fluoro-2-methyl-1-(4-methylthiobenzylidene)-3-indanacetonitrile with a yield of 83.8%.

2.0 g of ammonium metatungstate was dissolved in 8.0 g of water to form a solution. 10 g of the solution, 10 g of a SBA-15 mesoporous material, and 200 mL of n-hexane were introduced into a reaction vessel. This mixture was stirred at room temperature for 3 hours followed by filtration and oven dried to obtain 12 g of a powder. 12 g of the powder was mixed with 12 g of tellurium powder. This mixture was introduced into a tube furnace, and subjected to a reduction reaction at 700° C. for 2 hours with hydrogen being introduced into the furnace (with a hydrogen flow rate of 200 mL/min). A solid obtained was added into 100 mL of 30% HF solution. The solution was stirred at 25° C. for 2 hours, and then filtered to obtain a solid. After drying the solid, 1.99 g of a catalyst was obtained.

50 g of 5-fluoro-2-methyl-1-(4-methylthiobenzylidene)-3-indanacetonitrile, 1.0 g of the $WS_2$ catalyst, and 500 g of 60 wt % acetic acid aqueous solution were introduced into a reaction vessel to proceed with a reaction at 50 to 55° C. for 8 hours under visible light irradiation. At the end of the reaction, the catalyst was recovered by filtration, and the solvent in a filtrate obtained was recovered by distillation. The distillation was carried out at 110° C. for 1 h, precipitating a crude product. The crude product was subjected to filtration to give a filter cake. The filter cake was recrystallized in 80 g of isopropanol at 82° C. for 4 hours, to give 49.9 g of sulindac with a purity of 99.5% and a yield of 90.0%. A mass ratio of the Z-isomer of the sulindac product to its E-isomer was Z/E=99.3:1.

Example 6

164 g of 6-fluoro-2-methylindanone, 100 g of cyanoacetic acid, 10 g of potassium acetate, and 1000 g of xylene were introduced into a reaction vessel fitted with a thermometer, a stirrer, and a water separator. During the reaction, the reaction temperature was controlled at 120 to 135° C., and the reaction was carried out with removing water produced by the reaction by fractional distillation from the reaction system. After 15 hours of reaction, the reaction solution was cooled to 50° C., and 44 g of potassium hydride and 160 g of 4-(methylthio)benzaldehyde were then added into the reaction solution. The reaction solution was kept at 60° C. for 8 hours, then adjusted to neutral with 0.1 M hydrochloric acid and subjected to layer separation. An organic layer formed was evaporated at 135° C. for 1 h to dryness. A crude product obtained was recrystallized in 500 g of ethyl acetate at 78° C. for 4 h to obtain 275.9 g of 5-fluoro-2-methyl-1-(4-methylthiobenzylidene)-3-indanacetonitrile with a yield of 86.0%. 2.0 g of ammonium molybdate was dissolved in 8.0 g of water to form a solution. 10 g of the solution, 10 g of a SBA-15 mesoporous material, and 200 mL of n-hexane were introduced into a reaction vessel. This mixture was stirred at room temperature for 3 hours followed by filtration and oven dried to obtain 12 g of a powder. 12 g of the powder was mixed with 12 g of tellurium powder. This mixture was introduced into a tube furnace, and subjected to a reduction reaction at 700° C. for 2 hours with hydrogen being introduced into the furnace (with a hydrogen flow rate of 200 mL/min). A solid obtained was added into 100 mL of 30% HF solution. The solution was stirred at 25° C. for 2 hours, and then filtered to obtain a solid. After drying the solid, 2.27 g of a catalyst was obtained.

50 g of 5-fluoro-2-methyl-1-(4-methylthiobenzylidene)-3-indanacetonitrile, 1.0 g of the $Mo_3S_2Se_4$ catalyst, 500 g of 50 wt % acetic acid aqueous solution were introduced into a reaction vessel to proceed with a reaction at 60 to 65° C. for 6 hours under visible light irradiation. At the end of the reaction, the catalyst was recovered by filtration, and the solvent in a filtrate obtained was recovered by distillation. The distillation was carried out at 110° C. for 1 h, precipitating a crude product. The crude product was subjected to filtration to give a filter cake. The filter cake was recrystallized in 80 g of isopropanol at 82° C. for 4 hours, to give 54.4 g of sulindac with a purity of 99.5% and a yield of 98.1%. A mass ratio of the Z-isomer of the sulindac product to its E-isomer was Z/E=99.2:1.

The invention is described above based on preferable embodiments. It will be apparent to those skilled in the art that various improvements and embellishments can be made without departing from the concept of the invention.

The invention claimed is:

1. A process for preparing 5-fluoro-2-methyl-1-(4-methylthiobenzylidene)-3-indanacetonitrile, comprising:
    mixing 6-fluoro-2-methyl-1-indanone, cyanoacetic acid, a first organic solvent and an acetic acid-based catalyst to proceed with a first condensation reaction to give a first condensation reaction solution, which contains 5-fluoro-2-methyl-3-indanacetonitrile; and
    mixing the first condensation reaction solution, per se, with a base, a second organic solvent and 4-(methylthio)benzaldehyde to proceed with a second condensation reaction to give 5-fluoro-2-methyl-1-(4-methylthiobenzylidene)-3-indanacetonitrile.

2. The process according to claim 1, wherein the first condensation reaction is carried out at 100 to 140° C. for 5 to 30 hours.

3. The process according to claim 1, wherein the second condensation reaction is carried out at 50 to 90° C. for 3 to 8 hours.

4. The process according to claim 1, wherein the base comprises one or more of: sodium hydroxide, sodium ethoxide, sodium methylate, potassium hydroxide, sodium hydride and potassium hydride.

5. The process according to claim 1, further comprising: after the second condensation reaction, subjecting a product of the second condensation reaction to cooling, pH adjustment, layer separation, evaporation of an organic layer and purification sequentially.

6. A process for preparing sulindac, comprising:
    preparing 5-fluoro-2-methyl-1-(4-methylthiobenzylidene)-3-indanacetonitrile according to claim 1, and
    mixing 5-fluoro-2-methyl-1-(4-methylthiobenzylidene)-3-indanacetonitrile with a solvent and a photocatalyst to proceed with a photo-catalytic oxidation and hydrolysis reaction under light irradiation to give sulindac,
    wherein, the photocatalyst is a metal chalcogenide nanomesh, the metal chalcogenide having a formula MX2, where M represents one or more of Mo, W and V, and X represents one or more of S, Se and Te.

7. A process for preparing sulindac, comprising:
    preparing 5-fluoro-2-methyl-1-(4-methylthiobenzylidene)-3-indanacetonitrile according to claim 2, and
    mixing 5-fluoro-2-methyl-1-(4-methylthiobenzylidene)-3-indanacetonitrile with a solvent and a photocatalyst to proceed with a photo-catalytic oxidation and hydrolysis reaction under light irradiation to give sulindac,
    wherein, the photocatalyst is a metal chalcogenide nanomesh, the metal chalcogenide having a formula MX2, where M represents one or more of Mo, W and V, and X represents one or more of S, Se and Te.

8. A process for preparing sulindac, comprising:
    preparing 5-fluoro-2-methyl-1-(4-methylthiobenzylidene)-3-indanacetonitrile according to claim 3, and
    mixing 5-fluoro-2-methyl-1-(4-methylthiobenzylidene)-3-indanacetonitrile with a solvent and a photocatalyst to proceed with a photo-catalytic oxidation and hydrolysis reaction under light irradiation to give sulindac,
    wherein, the photocatalyst is a metal chalcogenide nanomesh, the metal chalcogenide having a formula MX2, where M represents one or more of Mo, W and V, and X represents one or more of S, Se and Te.

9. A process for preparing sulindac, comprising:
    preparing 5-fluoro-2-methyl-1-(4-methylthiobenzylidene)-3-indanacetonitrile according to claim 4, and
    mixing 5-fluoro-2-methyl-1-(4-methylthiobenzylidene)-3-indanacetonitrile with a solvent and a photocatalyst to proceed with a photo-catalytic oxidation and hydrolysis reaction under light irradiation to give sulindac,
    wherein, the photocatalyst is a metal chalcogenide nanomesh, the metal chalcogenide having a formula MX2, where M represents one or more of Mo, W and V, and X represents one or more of S, Se and Te.

10. A process for preparing sulindac, comprising:
    preparing 5-fluoro-2-methyl-1-(4-methylthiobenzylidene)-3-indanacetonitrile according to claim 5, and
    mixing 5-fluoro-2-methyl-1-(4-methylthiobenzylidene)-3-indanacetonitrile with a solvent and a photocatalyst to proceed with a photo-catalytic oxidation and hydrolysis reaction under light irradiation to give sulindac,
    wherein, the photocatalyst is a metal chalcogenide nanomesh, the metal chalcogenide having a formula MX2, where M represents one or more of Mo, W and V, and X represents one or more of S, Se and Te.

11. The process according to claim 6, further comprising: after the photo-catalytic oxidation and hydrolysis reaction, subjecting a product of the reaction to a first filtration, distillation, a second filtration and purification sequentially.

12. The process according to claim 7, further comprising: after the photo-catalytic oxidation and hydrolysis reaction, subjecting a product of the reaction to a first filtration, distillation, a second filtration and purification sequentially.

13. The process according to claim 8, further comprising: after the photo-catalytic oxidation and hydrolysis reaction, subjecting a product of the reaction to a first filtration, distillation, a second filtration and purification sequentially.

14. The process according to claim 9, further comprising: after the photo-catalytic oxidation and hydrolysis reaction, subjecting a product of the reaction to a first filtration, distillation, a second filtration and purification sequentially.

15. The process according to claim 10, further comprising: after the photo-catalytic oxidation and hydrolysis reaction, subjecting a product of the reaction to a first filtration, distillation, a second filtration and purification sequentially.

16. The process according to claim 6, wherein the photo-catalytic oxidation and hydrolysis reaction is carried out at 20 to 80° C. for 2 to 12 hours.

17. The process according to claim 7, wherein the photo-catalytic oxidation and hydrolysis reaction is carried out at 20 to 80° C. for 2 to 12 hours.

18. The process according to claim 8, wherein the photo-catalytic oxidation and hydrolysis reaction is carried out at 20 to 80° C. for 2 to 12 hours.

19. The process according to claim 6, wherein a mass ratio of the photocatalyst to 5-fluoro-2-methyl-1-(4-methylthio-benzylidene)-3-indanacetonitrile is from 0.5%: 1 to 3%: 1.

20. The process according to claim 6, wherein the solvent is an acetic acid solution with a mass ratio of acetic acid to water being from about 0.25:1 to 4:1.

\* \* \* \* \*